US010660589B2

(12) United States Patent
Roessl

(10) Patent No.: US 10,660,589 B2
(45) Date of Patent: May 26, 2020

(54) BASELINE SHIFT DETERMINATION FOR A PHOTON DETECTOR

(71) Applicant: KONINKLIJKE PHILIPS N.V., Eindhoven (NL)

(72) Inventor: Ewald Roessl, Ellerau (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 224 days.

(21) Appl. No.: 15/534,528

(22) PCT Filed: Dec. 10, 2015

(86) PCT No.: PCT/EP2015/079181
§ 371 (c)(1),
(2) Date: Jun. 9, 2017

(87) PCT Pub. No.: WO2016/096580
PCT Pub. Date: Jun. 23, 2016

(65) Prior Publication Data
US 2017/0322329 A1 Nov. 9, 2017

(30) Foreign Application Priority Data

Dec. 16, 2014 (EP) .................................... 14198239

(51) Int. Cl.
*A61B 6/03* (2006.01)
*G01T 1/24* (2006.01)
(Continued)

(52) U.S. Cl.
CPC ............ *A61B 6/4241* (2013.01); *A61B 6/032* (2013.01); *A61B 6/42* (2013.01); *A61B 6/4208* (2013.01);
(Continued)

(58) Field of Classification Search
CPC ......... A61B 6/032; A61B 6/42; A61B 6/4208; A61B 6/4233; A61B 6/4241; A61B 6/482;
(Continued)

(56) References Cited

U.S. PATENT DOCUMENTS 3,800,143 A     3/1974   Fishman
4,055,766 A *   10/1977   Miller .................. G01T 1/1642
                                                         250/363.02
(Continued)

FOREIGN PATENT DOCUMENTS

GB            2023814          1/1980
JP             2006305228      11/2006
(Continued)

OTHER PUBLICATIONS

Thomas Friese, "An Analog Spectrum Stabilizer", RAPP EUR-4289E ISPRA Nuclear Electronics Symposium, May 6, 1969.

*Primary Examiner* — Allen C. Ho
(74) *Attorney, Agent, or Firm* — Larry Liberchuk

(57) ABSTRACT

The present invention relates to determining baseline shift of an electrical signal generated by a photon detector (102) of an X-ray examination device (101). For this purpose, the photon detector comprises a processing unit (103) that is configured to determine a first crossing frequency of a first pulse height threshold by the electrical signal generated by the photon detector. The first pulse height threshold is located at a first edge of a noise peak in the pulse height spectrum of the electrical signal.

12 Claims, 3 Drawing Sheets

(51) Int. Cl.
  *A61B 6/00* (2006.01)
  *G01T 1/40* (2006.01)
  *G01T 7/00* (2006.01)
  *H05G 1/30* (2006.01)

(52) U.S. Cl.
  CPC ............ *A61B 6/4233* (2013.01); *A61B 6/482* (2013.01); *A61B 6/52* (2013.01); *A61B 6/5205* (2013.01); *A61B 6/58* (2013.01); *A61B 6/582* (2013.01); *A61B 6/585* (2013.01); *A61B 6/586* (2013.01); *G01T 1/24* (2013.01); *G01T 1/40* (2013.01); *G01T 7/005* (2013.01); *H05G 1/30* (2013.01)

(58) Field of Classification Search
  CPC ........... A61B 6/52; A61B 6/5205; A61B 6/58; A61B 6/582; A61B 6/585; A61B 6/586; G01T 1/24
  USPC .......... 378/5, 19, 91, 98.8, 98.9, 98.11, 207; 250/370.09
  See application file for complete search history.

(56) References Cited

U.S. PATENT DOCUMENTS

| | | | | |
|---|---|---|---|---|
| 5,449,897 | A * | 9/1995 | Bertelsen | G01T 1/1642 250/207 |
| 5,532,944 | A | 7/1996 | Battista | |
| 5,774,522 | A * | 6/1998 | Warburton | G01T 1/171 250/370.06 |
| 5,873,054 | A * | 2/1999 | Warburton | G01T 1/171 250/370.06 |
| 6,609,075 | B1 * | 8/2003 | Warburton | G01T 1/17 702/22 |
| 6,822,506 | B2 * | 11/2004 | Binkley | H03K 5/1536 327/551 |
| 7,157,715 | B1 * | 1/2007 | Crain, Jr. | G01T 1/026 250/370.07 |
| 7,634,061 | B1 * | 12/2009 | Tümer | G01T 1/247 378/62 |
| 7,763,859 | B2 * | 7/2010 | Mott | G01T 1/171 250/369 |
| 7,807,973 | B2 * | 10/2010 | Mott | G01T 1/17 250/361 R |
| 7,855,370 | B2 * | 12/2010 | Mott | G01T 1/171 250/370.06 |
| 7,924,079 | B2 | 4/2011 | Schmand | |
| 8,039,787 | B2 * | 10/2011 | Mott | G01R 29/02 250/252.1 |
| 8,262,288 | B2 * | 9/2012 | Shaughnessy | A61B 6/032 378/154 |
| 8,340,377 | B2 * | 12/2012 | McFarland | A61B 6/032 250/363.03 |
| 8,350,221 | B2 * | 1/2013 | Steadman Booker | G01T 1/17 250/336.1 |
| 8,384,038 | B2 * | 2/2013 | Guo | G01T 1/247 250/370.09 |
| 8,723,132 | B2 * | 5/2014 | Baeumer | G01T 1/2018 250/370.11 |
| 8,754,376 | B2 * | 6/2014 | Arseneau | A61B 6/5258 250/369 |
| 8,907,290 | B2 * | 12/2014 | Kim | A61B 6/03 250/363.03 |
| 8,941,076 | B2 * | 1/2015 | Abraham | G01T 1/171 250/336.1 |
| 9,176,238 | B2 * | 11/2015 | Herrmann | G01T 1/17 |
| 9,268,035 | B2 * | 2/2016 | Herrmann | G01T 1/17 |
| 9,301,378 | B2 * | 3/2016 | Steadman Booker | G01T 1/24 |
| 9,504,438 | B2 * | 11/2016 | Proksa | G01T 1/24 |
| 9,759,822 | B2 * | 9/2017 | Daerr | G01T 1/17 |
| 9,784,854 | B2 * | 10/2017 | Blevis | G01T 1/18 |
| 10,001,567 | B2 * | 6/2018 | Roessl | G01T 1/24 |
| 2002/0085667 | A1 | 7/2002 | Miller | |
| 2013/0284940 | A1 | 10/2013 | Herrmann | |

FOREIGN PATENT DOCUMENTS

| | | |
|---|---|---|
| SU | 1146091 | 3/1985 |
| WO | 2011127469 | 10/2011 |
| WO | 2012095710 | 7/2012 |
| WO | 2013057645 | 4/2013 |
| WO | 2013061186 | 5/2013 |
| WO | 2014057400 | 4/2014 |
| WO | 2014087264 | 6/2014 |
| WO | 2014091278 | 6/2014 |

* cited by examiner

BASELINE SHIFT DETERMINATION FOR A PHOTON DETECTOR

CROSS REFERENCE TO RELATED APPLICATIONS

This application is the U.S. National Phase application under 35 U.S.C. § 371 of International Application No. PCT/EP2015/079181, filed Dec. 10, 2015, published as WO 2016/096580 on Jun. 23, 2016, which claims the benefit of European Patent Application Number 14198239.7 filed Dec. 16, 2014. These applications are hereby incorporated by reference herein.

FIELD OF THE INVENTION

The present invention relates to the determination of the baseline shift of a photon detector. In particular, the present invention relates to a processing unit, a photon detector, an X-ray examination device, a method, a program element, and a computer-readable medium.

BACKGROUND OF THE INVENTION

Photon counting detector performance can be severely degraded at high X-ray flux due to uncontrollable and unpredictable changes in the baseline of the analogue signal of the photon counting detector and probed by the readout ASIC. These changes in the baseline can be induced, for example, by changes in the resistivity of the sensor material upon intense X-ray irradiation, changes in the electric field due to space charge or other effects in the semiconductor and can depend on the irradiation history as well.

SUMMARY OF THE INVENTION

There may be a need to provide for a more precise determination of the baseline shift of the signal generated by a photon detector.

Aspects of the invention are stated in the independent claims. Advantages and further embodiments are set out in the dependent claims, the description and the figures.

A first aspect of the invention relates to a processing unit for processing an electrical signal generated by a photon detector of an X-ray examination device. The processing unit is configured to determine a baseline shift of the electrical signal by determining a change of a first rate of exceeding a first pulse height threshold by the electrical signal. The first pulse height threshold is a pulse height at a first edge of a noise peak in a pulse height spectrum of the electrical signal.

In other words, the gist of the invention may be seen in continuously monitoring the effect of a baseline shift or drift such that the baseline shift can either be corrected in real time by a baseline restorer or can be included in the detectors output as a means to correct the signal of the detector by means of subsequent processing. The baseline shift can be detected very sensitively by measuring the changes in a crossing frequency of a pulse height threshold, i.e. the first pulse height threshold. By setting the first pulse height threshold at the first edge of the noise peak, a baseline shift will cause the first rate of exceeding the first pulse height threshold to decrease or to increase rapidly. Thus, a very precise measure of the current level of the baseline shift can be obtained from the change of the first rate.

The invention is based on the knowledge that there are several issues with photon detectors, in particular with semiconductors, that may influence the signal quality of the photon detector. A collection of such effects may be summarized under the term "polarization". In a simplified picture of polarization, the number of electron-hole pairs generated under intense irradiation of the semiconductor detector with X-rays becomes so large that even under the influence of a strong electric field, the collection efficiency of the sensor might be insufficient to quickly transport the charges out of the sensor. In this situation, regions might form in certain sensor parts where the local charge density affects the local electric field and, hence, the charge collection efficiency of the sensor is compromised. Other effects which are not induced by radiation, for example, dark current versus photo current, may have an influence on the DC current in the sensor.

Moreover, when the DC component of the analogue signal received by one channel of the readout ASIC (processing unit) is subject to dynamic changes, the pulse height measurements of all pulses may be subject to such errors. This effect may significantly impact the image quality of the X-ray examination device when they are left uncorrected. Furthermore, this effect may lead to a time dependence of the measured number of photons in a certain one-sided or two-sided energy window even under conditions of constant illumination.

In the context of the present invention, the processing unit may refer to a readout unit or a readout ASIC (application-specific integrated circuit) of the photon detector. The photon detector may be an X-ray detector. Moreover, the photon detector may be realized as a photon counting detector. Thus, the photon detector may be configured to count incoming events that cause a pulse that exceeds a certain pulse height threshold value. It may be understood that an event may relate to an incoming photon on the photon detector. The photon detector may be configured to generate the electrical signal in response to such an event. Thus, the electrical signal may be understood to be an electrical response signal to the incoming event.

This electrical signal may be subject to a baseline shift or a baseline drift. The baseline may refer to a DC component of the electrical signal of the photon detector as it is described above. As described above, the baseline may be drifting over time. The baseline shift may be determined by determining the baseline or by determining the change of the baseline. Thus, it may be understood that the determination of the baseline shift may comprise the determination of the baseline at different points in time. In order to correctly identify the height of the signal pulse occurring at a time t, the processing unit may be configured to determine the baseline at the same time t, i.e. the baseline may be determined as a function of time, b(t). In other words, in case the energy thresholds were for example calibrated with respect to a baseline b=0, a baseline shift at a time t amounting to $b(t)=b_0$ will lead to a misidentification of the pulse height by the very same amount $b_0$. Thus, by determining the value $b_0$, the measured pulse height can be corrected even after the erroneous measurement.

It may be understood that determining the change of the first rate of exceeding the first pulse height threshold by the electrical signal may relate to determining the number of crossings of the first pulse height threshold by the electrical signal, and/or to comparing the determined number with a reference value for the number of pulses. A crossing of the first pulse-height threshold may be caused by a pulse or by a noise component of the electrical signal. In the context of the present invention, the rate of exceeding a pulse height threshold can also be denoted as the crossing frequency of the pulse height threshold.

The pulse height spectrum may refer to the rate or frequency of exceeding or crossing a pulse height threshold by the electrical signal as a function of the pulse height threshold. For example, the pulse height spectrum may be an integrated pulse height spectrum. The noise peak may be positioned at the lower pulse height end of the pulse height spectrum and may have a Gaussian shape. The first edge may refer to a rising or falling edge of the noise peak. For example, the first edge is the rising, left edge of the noise peak, i.e. the edge of the noise peak that is located at smaller pulse heights compared to the falling, right edge of the noise peak.

The noise peak may at least partly be caused by an electronic circuit of the detector and/or the processing unit. Moreover, the noise peak may the peak which is located around the lowest pulse height threshold in the pulse height spectrum. In other words, there may be no peak that is positioned around a lower pulse height threshold than the noise peak.

Moreover, the processing unit may be configured to determine the baseline shift during the operation of the photon detector. Thus, the baseline shift determination may be performed during the frame reading of the photon detector. For example, the processing unit may be configured to determine the baseline shift for every frame, for every fifth frame, or for every tenth frame of the photon detector reading. In this respect, a distinction may be made between two cases, irradiation of the photon detector at low flux, where pile up effects may be less important, and irradiation of the photon detector at high flux, where pile up effects may be more significant. A pile up effect may relate to a situation of the photon detector, where several events occur at the same time or in a short amount of time such that they are not distinguishable. In the low flux case, the detector may be idle most of the time and the baseline shift may be determined during the time periods between the pulses. For example, the baseline shift may be determined by triggering the baseline shift determination described in the context of the invention at the completion of the processing of one pulse. In this case, some pulses within one frame may be corrected differently than other pulses such that the height of the pulse may be corrected immediately before information is lost, for example, by incrementing a counter. The baseline shift may alternatively be determined at the beginning or the end of each frame. Moreover, in the low-flux case, the left edge crossing frequency can be indicative of the base line shift on a frame per frame level.

In the high flux case, the instances in time where the analogue signal of the photon detector is dominated by the baseline may become rare. Hence, in this case, a control unit may be provided that is configured to switch off the X-ray source of the X-ray examination device during certain time periods during which an assessment or determination of the baseline may be performed. For example, the X-ray source may be turned off by shutters or grid switching options provided in the X-ray source. This switching of the X-ray source is preferably, but not necessarily, synchronized with the frame readout of the X-ray detector or system.

According to a further exemplary embodiment, the first edge is a rising edge of the noise peak. Thus, the first edge may be associated to lower pulse height thresholds compared to the falling edge of the noise peak.

By selecting a pulse height threshold located at the rising edge of the noise peak, the determined change of the rate of crossing the first determined pulse height threshold is less influenced by the X-ray signal component.

According to a further exemplary embodiment of the invention, the processing unit is further configured to determine the baseline shift of the electrical signal by determining a change of a second rate of exceeding a second pulse height threshold of the electrical signal. The second pulse height threshold is a pulse height at a second edge of the noise peak in the pulse height spectrum of the electrical signal. Furthermore, the second edge is a falling edge of the noise peak. Thus, the second edge may be associated to greater pulse height thresholds compared to the rising edge of the noise peak.

Moreover, the features and advantages described with respect to the first rate and the first pulse height threshold may also apply to the second rate and the second pulse height threshold. By measuring two rates of exceeding two pulse height thresholds, the baseline shift may be determined more precisely. Furthermore, the use of two thresholds can increase the dynamic range of the baseline shift determination, i.e. the allowed range of the admissible amplitudes of the shifts.

According to a further exemplary embodiment of the invention, the processing unit is configured to determine a first reference value for the first rate. Furthermore, the processing unit is configured to determine the change of the first rate by subtracting a currently measured rate of exceeding the first pulse height threshold by the electrical signal from the first reference value.

Hereby, the currently measured rate of exceeding the first pulse height threshold may refer to the rate of exceeding the first pulse height threshold during the readout frame of the photon detector. The processing unit may be configured to determine the first reference value at a first period and to determine the change at a second period, which second period may be during the readout frame of the photon detector.

According to a further exemplary embodiment of the invention, the processing unit is configured to perform a threshold scan of the electrical signal for determining the pulse height spectrum of the electrical signal. Furthermore, the processing unit is configured to set the first reference point at an inflection point of an edge of the noise peak of the determined pulse height spectrum.

Moreover, the processing unit may also be configured to perform a threshold scan of the electrical signal for determining the pulse height spectrum of the electrical signal and to set the reference point at another position of the edge of the noise peak. The threshold scan may refer to determining the number of pulses which exceed or cross a certain pulse height threshold, thereby scanning different pulse height thresholds. The threshold scan may yield an integrated pulse height spectrum. By setting the first reference point at an inflection point, a linear approximation of the baseline shift may yield a precise value for the baseline shift.

According to a further exemplary embodiment of the invention, the processing unit is configured to subtract the baseline shift from the electrical signal.

In other words, the processing unit may comprise an additional hardware scheme which may actively compensate the baseline as a function of the latest sample of the baseline. For example, the processing unit may comprise a baseline restore circuit. For example, the determination of the baseline shift may be performed before a frame reading of the detector such that the electrical signal of the detector can be corrected online. For example, the thresholds may be set by means of a digital-to-analogue-converter-unit (DAC) to correspond to pulse-height values which relate to predefined energy values. The DAC may convert a user-defined digital energy value (e.g. an integer multiple of keV) into an analogue voltage level corresponding to the pulse-height corresponding to that energy. Based on the determination of the base-line shift, the DAC of all thresholds of the processing unit may be shifted by the amount of the determined baseline shift.

According to a further exemplary embodiment of the invention, the processing unit is configured to store the determined baseline shift for different points in time in a storage unit.

The storage unit may, for example, be a memory unit. In this way, a software unit processing the output of the processing unit can correct the output of the processing unit with the stored baseline shift.

According to a further exemplary embodiment of the invention, the processing unit is configured to determine the baseline shift on the basis of a functional relation between the baseline shift and the change of the first rate.

Furthermore, if the processing unit is configured to determine a second rate as described above, the processing unit is also configured to determine the baseline shift on the basis of a functional relation between the baseline shift and the change of the second rate.

This functional relation may for example be a linear relation between the baseline shift and the change of the first rate:

$$b(t)=b_0+c[H-H(p^-)],$$

where $b(t)$ denotes the currently determined baseline, $b_0$ the initial value of the baseline, c the constant of proportionality between the baseline and the change of the crossing frequency, H the reference value of the first rate of exceeding the first pulse height threshold (first crossing frequency), and $H(p^-)$ the currently determined first rate of exceeding the first pulse height threshold $p^-$ (first crossing frequency). In other words, $[H-H(p^-)]$ denotes the change of the first rate (first crossing frequency). However, the functional relation may also comprise higher order terms or more complex functions.

A second aspect of the invention relates to a photon detector for an X-ray examination device comprising a processing unit described in the context of the present invention. As described above, the photon detector may be an X-ray detector, advantageously a photon counting detector.

A third aspect of the invention relates to an X-ray examination device comprising the photon detector described in the context of the present invention.

The X-ray examination device may for example be a CT scanner. Moreover, the X-ray examination device may be a device for performing spectral CT scans or spectral mammography scans. However, the X-ray examination device may also refer to other kinds of X-ray examination devices.

According to a further exemplary embodiment of the invention, the X-ray examination device further comprises an X-ray source and a control unit for turning off the X-ray source when the processing unit determines the baseline shift.

The control unit may, for example, be a shutter or a grid switching device of the X-ray source. In this way, it is ensured that the change of the first rate is indicative of a true baseline shift unaffected by X-ray incidents at that very moment in time. For example, periods may be introduced in the measurement process where the X-ray source is turned off such that the baseline shift is determined during said periods. For example, for typical CT frame times of about 400 µs, a 10 µs period, in which the X-ray source is turned off, may be sufficient for determining the baseline shift on a frame per frame basis with a sufficient high statistics. In other words, the X-ray source may be turned off for a small fraction of the frame time. For example, this fraction may be less than 10%, 5%, or 2.5% of the frame time.

A fourth aspect of the invention relates to a method for determining a baseline shift in an electrical signal of a photon detector of an X-ray examination device. The method comprises the step of determining a change of a first rate of exceeding a first pulse height threshold by the electrical signal, wherein the first pulse height threshold is a pulse height at a first edge of a noise peak in a pulse height spectrum of the electrical signal. Furthermore, the method comprises the step of determining the baseline shift of the electrical signal on the basis of the determined change of the first rate.

According to a further exemplary embodiment, the method comprises the step of determining a change of a second rate of exceeding a second pulse height threshold by the electrical signal, wherein the second pulse height threshold is a pulse height at a second edge of the noise peak in the pulse height spectrum of the electrical signal. Furthermore, the method comprises the step of determining the baseline shift of the electrical signal on the basis of the determined change of the second rate.

The method described in the context of the present invention may be executed by a processing unit described in the context of the invention. Furthermore, the features and advantages outlined with respect to the processing unit may also refer to the method described herein. Moreover, the method may also comprise steps that are described with respect to the processing unit.

A fifth aspect of the invention relates to a program element, which, when it is executed by a processing unit, instructs the processing unit to carry out the method of claim described herein.

The program element may for example be a program code that is loaded in a processing unit such that the processing unit is configured to carry out the method described in the context of the invention. Moreover, the program element may also refer to an update enabling a program element to carry out the method described in the context of the invention.

A sixth aspect of the invention relates to a computer-readable medium, on which a program element is stored, which, when it is executed by a processing unit, instructs the processing unit to carry out the method described in the context of the invention.

For example, the computer-readable medium may be a memory unit which is configured to extend the processing unit such that the processing unit is configured to carry out the method described herein.

These and other aspects of the present invention will be apparent from and elucidated with reference to the embodiments described hereinafter.

BRIEF DESCRIPTION OF THE DRAWINGS

The figures are schematic and may not be true to scale. If, in the following description, the same reference sign are used with respect to different figures, they refer to the same or similar elements. The same or similar elements may also be provided with different reference signs.

DETAILED DESCRIPTION OF EXEMPLARY EMBODIMENTS

Figure 1:
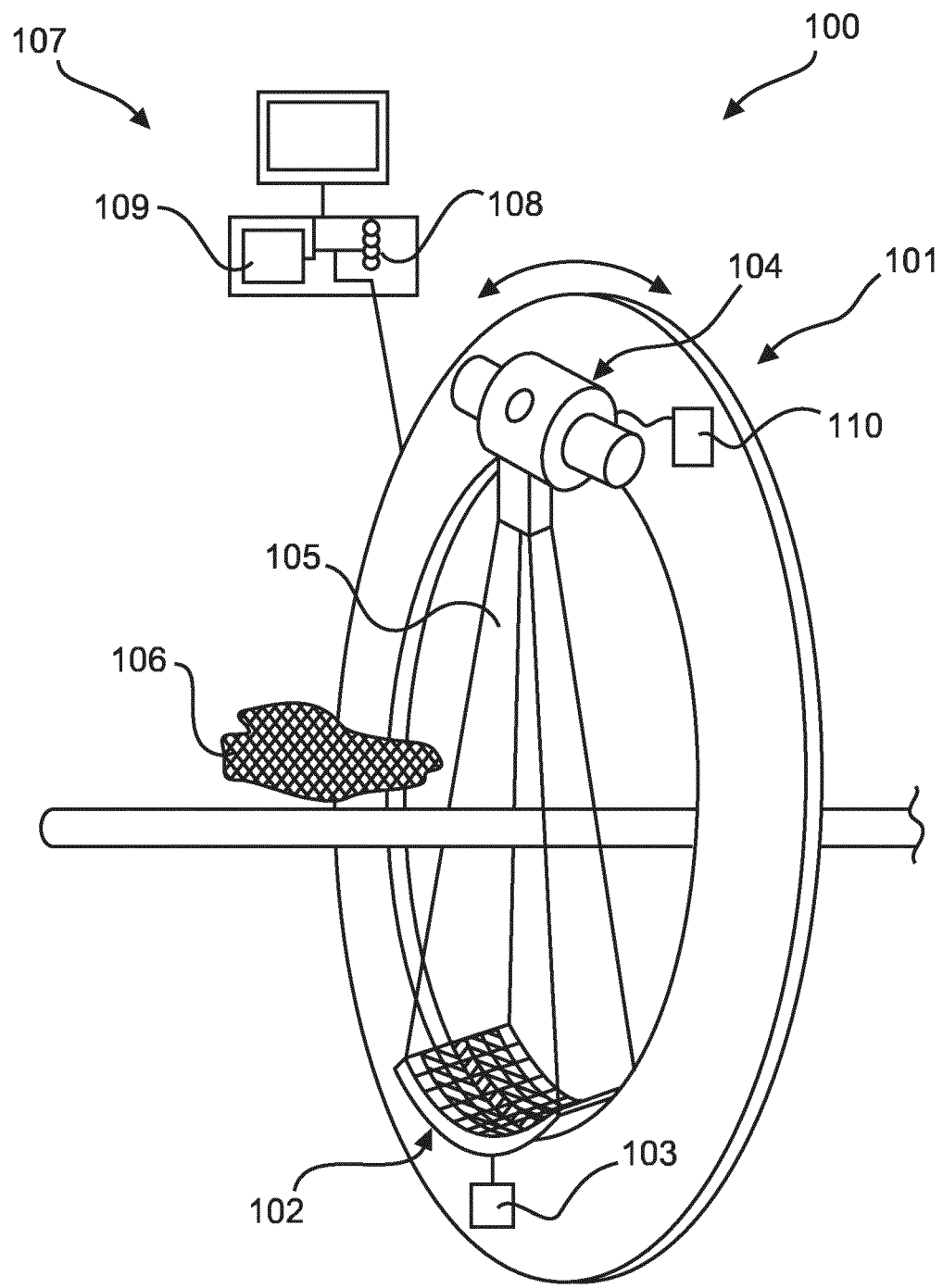
FIG. 1 shows an examination device comprising a photon detector and a processing unit according to an exemplary embodiment of the invention.

In FIG. 1, an X-ray examination device 100 according to an exemplary embodiment of the invention is shown. The X-ray examination device 100 comprises a gantry 101 which comprises an X-ray source 104 and a photon detector 102. The X-ray source 104 and the photon detector 102 can be rotated to different angular positions of the gantry 101 such that a probe 106 can be examined from different angles. The X-ray source 104 is configured to emit X-rays 105, which at least partly penetrate through the probe 106 and are detected by the photon detector 102. The photon detector 102 comprises a processing unit 103 for processing an electrical signal generated by the photon detector 102 of the X-ray examination device 100. The processing unit 103 is configured to determine a baseline shift of the electrical signal by determining a change of a first rate of exceeding a first pulse height threshold by the electrical signal. Furthermore, the first pulse height threshold is a pulse height at a first edge of a noise peak in a pulse height spectrum of the electrical signal.

The processing unit 103 can hereby actively compensate the baseline shift of the electrical signal or can store the baseline shift for different points in time on a storage unit 108 of a computer system 107 connected to the X-ray examination device 100. In this way, the processing unit 109 of the computer system 107 has access to the values of the baseline shift for the different points in time stored in the storage unit 108 such that the detector readout can be corrected by the software of the computer system 107 carried out by the processing unit 109.

Furthermore, the X-ray source comprises a control unit 110, for example a grid switching device or a shutter for turning on and off the X-ray source 104. In this way, the X-ray source 104 can be switched off for a short fraction of a readout frame of the photon detector 102 such that the baseline shift can be determined during this time.

Although an X-ray examination device 100 having a gantry 101 is shown, the X-ray examination device can also have another structure.

Figure 2:
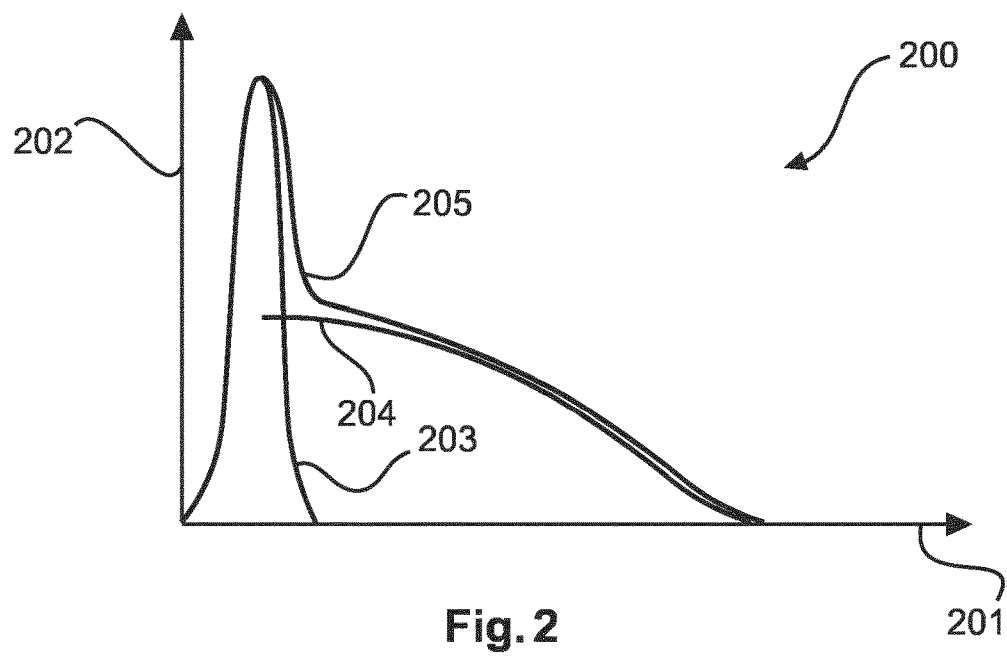
FIG. 2 shows a pulse height spectrum according to an exemplary embodiment of the invention.

In FIG. 2, a pulse height spectrum 200 according to an exemplary embodiment of the invention is shown. The pulse height spectrum 200 is a typical pulse height spectrum of a photon detector 102 of an X-ray examination device 100 described in the context of the invention. The x-axis 201 represents the pulse height thresholds and the y-axis 202 represents the rate of exceeding or crossing the pulse height threshold. In other words, the y-axis 202 represents the crossing frequencies for the different pulse height thresholds.

In this exemplary embodiment, the pulse height spectrum 200 is an integrated pulse height spectrum. Thus, for every pulse height threshold value, the total number of events or pulses exceeding or crossing the specific pulse height threshold value is shown. Since the electrical signal comprises a non-vanishing noise component, the pulse height spectrum 200 comprises a Gaussian noise peak 203. The signal of the detector induced by the X-rays of the X-ray source 104 is indicated by the signal 204. The complete signal comprising the Gaussian noise peak 203 and the signal 204 is shown by the curve 205. It can be assumed that the shape of the noise peak changes when the X-ray signal 204 is added to the Gaussian noise peak 203.

A greater noise component in the electrical signal would increase the full-width-half-maximum of the noise peak.

Figure 3:
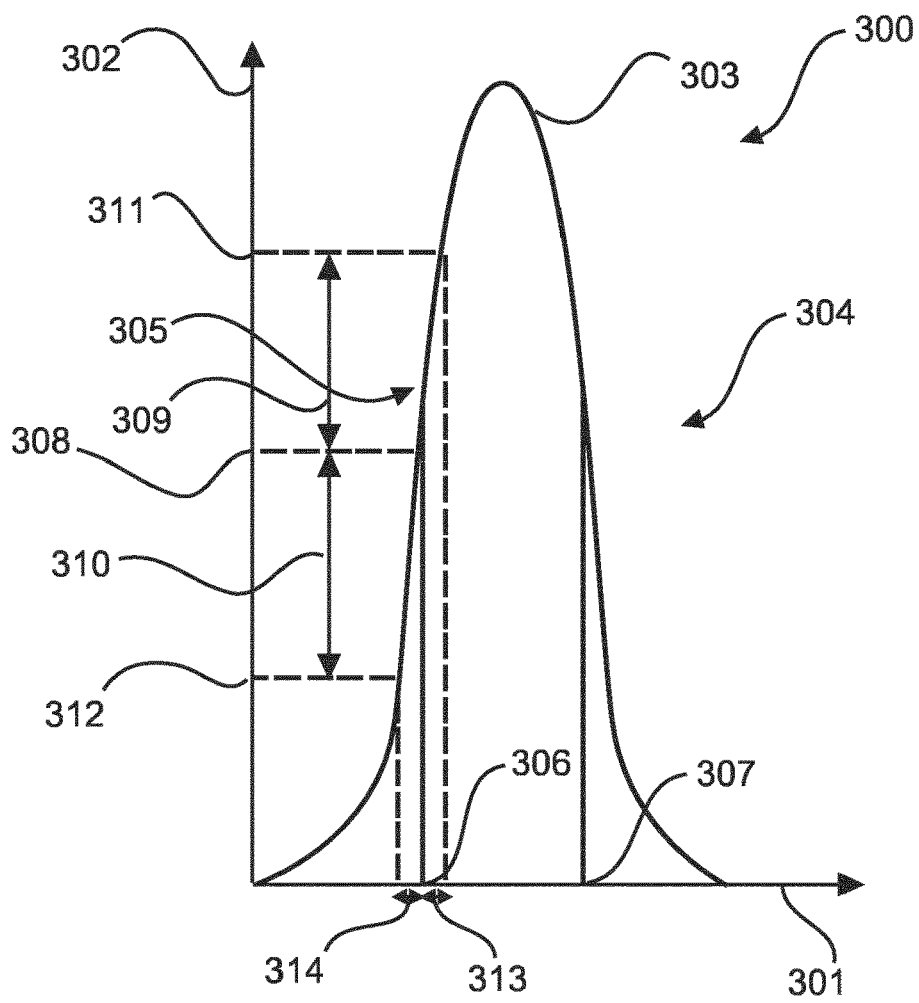
FIG. 3 shows a noise peak of a pulse height spectrum according to an exemplary embodiment of the invention.

In FIG. 3, a pulse height spectrum 300 of the electrical signal of the photon detector 102 according to an exemplary embodiment of the present invention is shown, when the X-ray source 104 is turned off. The X-axis 301 represents the pulse height threshold which is measured and the y-axis 302 represents the rate of exceeding or crossing said pulse height threshold. The Gaussian noise peak 303 is, for example, determined during a threshold scan, which is performed when the X-ray source 104 is turned off.

Since the X-ray source 104 is turned off, the pulse height spectrum 300 comprises only the Gaussian noise peak 303. The Gaussian noise peak 303 comprises a first, rising edge 305 and a second, falling edge 304. The position 306 at the x-axis 301 represents the first pulse height threshold p$^-$ and the position 307 at the x-axis 301 represents the second pulse height threshold p$^+$. The first pulse height threshold p. 306 is located at an inflection point of the first rising edge 305 of the Gaussian noise peak 303 and the second pulse height threshold p$^+$ 307 is located at an inflection point of the second falling edge 304 of the Gaussian noise peak 303.

The position 308 at the y-axis 302 indicates the first reference value H for the first rate of exceeding the first pulse height threshold H(p$^-$) 306 (first crossing frequency). Although not explicitly shown, a similar reference value for the second rate of exceeding the second pulse height threshold H(p$^+$) 307 (second crossing frequency) can be determined, which reference value of the second pulse height threshold H(p$^+$) can be of the same value as the reference value H of the first pulse height threshold H(p$^-$).

If during the operation of the photon detector 102, the baseline shift of the photon detector changes, a different rate of exceeding the first pulse height threshold H(p$^-$) 306 by the signal can be determined. For example, a greater rate 311 of exceeding the first pulse height threshold 306 relating to a positive change 309 of the first rate can be measured. However, also a lower rate 312 of exceeding the first pulse height threshold 306 can be measured, which represents a negative change 310 of the first rate.

Because of the steep gradient of the Gaussian noise peak 303 at the edges 305 and 304, the rates of crossing the first or second pulse height threshold 306, 307 strongly depends on the baseline shift of the electric signal. In other words, when the baseline shifts over time, the shift can be detected very sensitively by measuring the changes of the first or second rate.

The frequency of noise counts may be most sensitive to changes in the baseline when one or two thresholds are placed at the points 306 and/or 307 in the pulse height spectrum 300. For the first pulse height threshold 306, any positive baseline shift will cause the frequency to decrease rapidly whereas any negative baseline shift will cause a crossing frequency of the first pulse height threshold to increase rapidly.

To first order, the instantaneous baseline shift may be approximated as:

$$b(t)=b_0+c[H-H(p^-)],$$

where b(t) denotes the currently determined baseline, $b_0$ the initial value of the baseline, c the constant of proportionality between the baseline and the change of the crossing frequency, H the reference value of the first rate of exceeding the first pulse height threshold (first crossing frequency), and $H(p^-)$ the currently determined first rate of exceeding the first pulse height threshold $p^-$ (first crossing frequency). In other words, $[H-H(p^-)]$ denotes the change of the first rate (first crossing frequency). However, the functional relation may also comprise higher order terms. The values for $b_0$ and c may be determined during calibration of the photon detector.

It can be seen, that the changes of the first rates 311 and 312 strongly depend on the changes 314 and 313 of changes in the baseline.

Figure 4:
FIG. 4 shows a flow-chart of a method according to an exemplary embodiment of the invention.

In FIG. 4, a flow-chart for a method for determining a baseline shift in an electrical signal of a photon detector 102 of an X-ray examination device 100 according to an exemplary embodiment is shown. The method comprises the step S1 of determining a change of a first rate of exceeding a first pulse height threshold by the electrical signal, wherein the first pulse height threshold is a pulse height at a first edge of a noise peak in a pulse height spectrum of the electrical signal. Furthermore, the method comprises step S2 of determining the baseline shift of the electrical signal on the basis of the determined change of the first rate.

Figure 5:
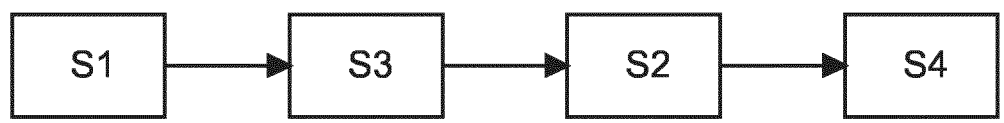
FIG. 5 shows a flow-chart of a method according to an exemplary embodiment of the invention.

In FIG. 5, a further flow-chart for a method for determining a baseline shift in an electrical signal of a photon detector 102 of an X-ray examination device 100 according to a further exemplary embodiment of the invention is shown. The method comprises step S1 of determining a change of a first rate of exceeding a first pulse height threshold by the electrical signal, wherein the first pulse height threshold is a pulse height at a first edge of a noise peak in a pulse height spectrum of the electrical signal. Furthermore, the method comprises step S3 of determining a change of a second rate of exceeding a second pulse height threshold by the electrical signal, wherein the second pulse height threshold is a pulse height at a second edge of the noise peak in the pulse height spectrum of the electrical signal. Furthermore, the method comprises step S2 of determining the baseline shift of the electrical signal on the basis of the determined change of the first rate and step S4 of determining the baseline shift of the electrical signal on the basis of the determined change of the second rate.

The invention has been illustrated and described in detail in the drawings and foregoing description, such illustration and description are to be considered illustrative and/or exemplary and not restrictive. The invention is not limited to the disclosed embodiments.

Other variations to the disclosed embodiments can be understood and affected by those skilled in the art in practicing the claimed invention, from a study of the drawings, the disclosure, and the appended claims. In the claims, the word "comprising" does not exclude other elements or steps and the indefinite article "a" or "an" does not exclude a plurality. The mere fact that certain measures are recited in mutually different dependent claims does not indicate that a combination of these measures cannot be used to advantage. A program element may be stored/distributed on a suitable medium, such as an optical storage medium or a solid state medium supplied together with or as a part of other hardware, but may also be distributed in other forms, such as via the Internet or other wired or wireless telecommunication systems. Any reference signs in the claims should not be construed as limiting the scope of the claims.

LIST OF REFERENCE SIGNS

100 X-ray examination device
101 gantry
102 photon detector
103 processing unit
104 X-ray source
105 X-rays
106 specimen
107 computer system
108 storage unit
109 processing unit of the computer system
110 control unit
200 pulse height spectrum
201 x-axis
202 y-axis
203 noise peak
204 x-ray signal
205 combined curve
300 pulse height spectrum
301 x-axis
302 y-axis
303 noise peak
304 falling edge
305 rising edge
306 first pulse height threshold $p^-$
307 second pulse height threshold $p^+$
308 reference value for the first rate H
309 positive change of the first rate
310 negative change of the first rate
311 greater first rate $H(p^-)$
312 smaller first rate $H(p^-)$
313 positive change of the baseline shift
314 negative change of the baseline shift

The invention claimed is:

1. A photon detector configured to detect a plurality of X-rays and generate an electrical signal, comprising:
a processor configured to:
process the electrical signal; and
determine a baseline shift of the electrical signal by determining a change of a first rate exceeding a first pulse height threshold by the electrical signal, wherein the first pulse height threshold is a pulse height at a first edge of a noise peak in a pulse height spectrum of the electrical signal.

2. The photon detector according to claim 1, wherein the first edge is a rising edge of the noise peak.

3. The photon detector according to claim 1, wherein the processor is further configured to determine the baseline shift of the electrical signal by determining a change of a second rate exceeding a second pulse height threshold of the electrical signal, wherein the second pulse height threshold is the pulse height at a second edge of the noise peak in the pulse height spectrum of the electrical signal, and wherein the second edge is a falling edge of the noise peak.

4. The photon detector according to claim 1, wherein the processor is further configured to determine a first reference value and subtract a currently measured rate of exceeding the first pulse height threshold by the electrical signal from the first reference value.

5. The photon detector according to claim 1, wherein the processor is further configured to:

perform a threshold scan of the electrical signal for determining the pulse height spectrum of the electrical signal; and set a first reference value at an inflection point of the first edge of the noise peak of the pulse height spectrum.

6. The photon detector according to claim 1, wherein the processor is configured to subtract the baseline shift from the electrical signal.

7. The photon detector according to claim 1, wherein the processor is configured to store the baseline shift for different points in time.

8. An X-ray device, comprising:
an X-ray source configured to emit a plurality of X-rays; and
a photon detector configured to detect the plurality of X-rays and generate an electrical signal, the photon detector comprising a processor configured to:
process the electrical signal; and
determine a baseline shift of the electrical signal by determining a change of a first rate exceeding a first pulse height threshold by the electrical signal, wherein the first pulse height threshold is a pulse height at a first edge of a noise peak in a pulse height spectrum of the electrical signal.

9. The X-ray device according to claim 8, further comprising a control processor configured to turn off the X-ray source when the processor determines the baseline shift.

10. A method for determining a baseline shift in an electrical signal of a photon detector of an X-ray examination device, the method comprising:

determining a change of a first rate exceeding a first pulse height threshold by the electrical signal, wherein the first pulse height threshold is a pulse height at a first edge of a noise peak in a pulse height spectrum of the electrical signal; and
determining the baseline shift of the electrical signal based on the change of the first rate.

11. The method according to claim 10, further comprising:
determining a change of a second rate exceeding a second pulse height threshold by the electrical signal, wherein the second pulse height threshold is a pulse height at a second edge of the noise peak in the pulse height spectrum of the electrical signal; and
determining the baseline shift of the electrical signal based on the change of the second rate.

12. A non-transitory computer-readable medium having one or more executable instructions stored thereon, which, when executed by a processor, cause the processor to perform a method for determining a baseline shift in an electrical signal of a photon detector of an X-ray examination device, the method comprising:
determining a change of a first rate exceeding a first pulse height threshold by the electrical signal, wherein the first pulse height threshold is a pulse height at a first edge of a noise peak in a pulse height spectrum of the electrical signal; and
determining the baseline shift of the electrical signal based on the change of the first rate.

* * * * *